United States Patent

Karsanov et al.

[11] Patent Number: 5,439,883
[45] Date of Patent: Aug. 8, 1995

[54] ANTIHYPOXIC FORMULATION

[76] Inventors: Nikolai V. Karsanov, ulitsa Gotua, 16, kv. 96; Evgenia V. Selikhova, prospekt Tsaritsy Tamary, 18, kv. 104; Nodar N. Kipshidze, ulitsa Sumbatashvili-Jushina, 9, kv. 2; Eteri I. Guchua, Digomsky massiv, 1 kvartal, korpus 11, kv. 5, all of Tbilisi, Georgia

[21] Appl. No.: 228,749

[22] Filed: Apr. 18, 1994

[51] Int. Cl.⁶ .................. A61K 31/455; A61K 31/52; A61K 38/42; A61K 31/70
[52] U.S. Cl. .............................. 514/6; 514/45
[58] Field of Search ............................ 514/645

[56] References Cited
FOREIGN PATENT DOCUMENTS 638315 2/1995 European Pat. Off. .

OTHER PUBLICATIONS

Karsanov et al VOPR. Med Khim 39/4:50–55 1993 B.A. 96:133243.
Karsanov et al 12V. Akad. Navk. Gvr2 SSR Ser Biol 9(5):230–241 BA 78.177882 (1990).
Irgashev et al Farmakol Tuksikol 51(5):41–44 Lgt Oct. 1988 Medline 89091415.
Zalewski et al Am. Heart J. 113(1):124–9 Jan 1987 Medline 87096959.
Snider et al Int. J. Sport. Nutr. 2(3):272–286 Sep. 1992 Medline 93230289.
Kostin et al Farmacol Toksikol 52(6):49–52 Nov. Dec. 1989 Medline 90/69029.

Primary Examiner—Shep K. Rose
Attorney, Agent, or Firm—Ladas & Parry

[57] ABSTRACT

The invention relates to cardiology, and provides an antihypoxic formulation, Energostim, including cytochrome C, nicotinamide adenine dinucleotide and inosine.

Energostim provides a complete normalization of energy metabolism and the recovery of oxygene deficiency in heart, brain, liver and other internals.

1 Claim, No Drawings

ANTIHYPOXIC FORMULATION

DESCRIPTION

1. Technical Field

The present invention relates to medicine, and more particularly it relates to the preparation of agents which provides the normalization of energy metabolism thereby eliminating oxygene-deficient conditions in heart, brain, liver and the like.

2. Background Art

A number of agents is known to have an antihypoxic activity, in particular cytochrome C which is referenced to here as the prior art.

With a 6-day coronary occlusion (CO) induced in dogs, a single medication of cytochrome C in a dosage of 2,5 mg/kg 15 min. after administration of it causes the improvement in tissue respiration and a considerable inhibition of necrotic process progression in the region of circulatory insufficiency while exertring no influence on the sizes of ischemic area (A. Zalevski et al., Am. Heart J., 1987, v. 113, no. 113, pp. 194–129).

The administration of cytochrome C in the increased amount of 5 mg/kg body weight, especially 10 mg/kg in a 2-hour coronary occlusion gives rise to normalization of ATP and creatine phosphate (CP) at extraischemic region of cardiac muscle and their considerable rise, and yet not to the normal, in the region of a circulatory insufficiency. This, in turn, leads to the improvement in myocardial function and structure (N. V. Kirsanov et al., Materialy Respublikanskoi nauchnoi conferentsii po enzimologii, Tbilisi, June, 1981).

The administration of cytochrome C in coronary occlusion within a 1–7 day period in a dosage of 10 mg/kg daily while increasing the level of adenyl nucleotides to the normal (by 1-3-th days) results in reduction of them to Control by the 7-th day (Sh. B. Irgashev, N. M. Yuldashev—Farmakol., toksikol., 1988, No. 5, p. 41–44).

The administration of cytochrome C in a dosage of 10 mg/kg in adrenaline/caffeine-mediated myocarditis returns the normal ATP and CP levels in rabbits (N. V.Karsanov, N. K. Khajdrava, Materialy II Vsesojuznogo simpoziuma po meditsinskoi enzimologii, Dushanbe, 1974). However, there is no rise in ADP and AMP, as compared to Control. This causes the increase in ATP/ADP ratio that, in turn, results in an endogenous inhibition of the Krebs cycle activity, especially if ATP content is above-normal.

The administration of cytochrome C in a much more dosage of 20 mg/kg for 14 days in a large-focal myocardial infarction which has not been complicated with power failure of the heart, and yet with a clinically expressed coronary insufficiency, makes it good in myocardial status at the periinfarction region and diminishes the sizes of necrotic area (B. I. Bezborodko, I. A. Shekhunov—Vrach. Delo, 1990, No. 8, p. 8–10).

Thus, cytochrome C, in either a single or a long-term medication, improves appreciably the energetic state at the region of myocardial ischemia, however it fails to provide a steady, equilibrium repair of cellular low-energy state and restore completely the homeostasis of the energy transfer system.

An object of the present invention is to provide a formulation, wherein the combination of its ingredients is directed to the elimination of cellular energy depletion (oxygen deficiency)-associated conditions, the restoration of steady state for normal function of the energy supply system by effecting simultaneously on the energy transfer systems and the cutting of time for attaining a stable medicinal effect, for example in case of myocarditis and coronary occlusion.

DISCLOSURE OF THE INVENTION

This problem is solved by including the activating agents as the ingredients of the formulation of the invention for three metabolic processes which will be distrupted most of all in the; complex system of a cellular energy exchange in oxygen deficiency-associated conditions: glycolysis (decrease in oxidation-reduction potential); oxidative phosphorylation (decrease in capacity of the electron transport through the chain of transferring them to oxygene), and de novo adenyl nucleotide synthesis, namely, cytochromc C (enzyme), nicotinamide-adenine dinucleotide (NAD) (coenzyme) and inosine (metabolite being the decomposition product of adenyl nucleotides) at the following mixture ratio parts by weight):

cytochrome C—10
NAD—0.5
inosine—80

The above formulation of the to the invention, known under the trade name "Energostim", shows his action not through the summation over all effects, and actually,it acts as a medicinal agent having novel properties—the capacity of ensuring a normal stable, equilibrium function of all the chains in the energy transfere system, that is the attainment of homeostasic state of the system, which will be disturbed in pathologic conditions and aggravated by a one-sided action.

The disturbance of a homeostatic state of the energy transfer system in a cellular oxygene deficiency, giving rise to a cellular low-energy state, is associated with considerable losses of cytochrome C and NAD in cells (Karsanov et al., 1981 and Table 1) and reduction in adenyl nucleotides in total (Table 2).

The reduction in mitochondrial cytochrome C causes the decrease in rate of electron transport to to oxygene. This, in turn, leads to decrease in rate of ATP production in the electron transport-coupled oxidative phosphorylation.

The reduction in cardiomyocyte ATP production is further associated with the decreased level of cellular NAD (in both cytosolic component andmitochondria). This, on the one hand, gives rise to the retardation of ATP production rate during the glycolytic reaction as well as the oxidative phosphorylation due to the decreased capacity of translocating proton from cytosole to mitochonria (via malate-aspartate shuttle), because of inhibiting the NAD-dependent glycolate dehydronenase activities and the glycolytic oxidoreduction and, on the other hand, it leads to the inhibition of the Krebs cycle NAD-dependent dehydrogenase activities.

The administration of cytochrome C in cellular oxygene deficiency-related conditions causes the inclusion cytochrom C into the mitochondrial membranes of the electron transport chain to oxygene (Karsanov et al., 1981) with subsequent reduction of them by passing through their transport chain. This provides the activation of ATP production by oxidative phosphorylation. As a result, ATP from an easily available energy source and its accumulation as CP rises to or near-normal (Tabl. 3). At this time, however, the levels of ADP and AMP does not rise greatly (allergic myocarditis), and the total content of adenyl nucleotides is still low (toxic-allergic myocarditis) or it increases slightly (adrenaline-mediated heart disease, Tabl. 4), or even it returns to the normal (allergic myocarditis, Tabl. 3).

However, the administration of cytochrome has no effects on NAD/NADH ratio (it remains to be shifted to NADH), except of that the total content of pyridine nucleotides increases (Tabl. 1). In view of this it may be safely suggested that the activities of NAD-dependent glycolate dehydrogenases and the Krebs cycle NAD-dependent dehydrogenases are changed slightlty under exposure to cytochrome C.

Thus, the action of cytochrome C only does not provide the complete restoration of a homeostatic state of the cellular energy transfer system.

The administration of NAD solely rises the level of myocardial ATP to the normal (allergic myocarditis and adrenaline-mediated heart failure, Tabl. 3 and 4), or near-normal (toxic and allergic myocarditis, Tabl. 2).

Since NAD administration causes the return of NAD/NADH ratio and their levels to the normal (Tabl. 4,5), its is reasonably to assume that the normalization of ATP is associated with the activation of NAD-dependent glycolate dehydrogenases, the glycolytic oxidoreduction and the translocation of proton from cytosole to mitochondria as well as the promotion of the Krebs cycle NAD-dependent dehydrogenase activities. However, the basic way of ATP production activation may be thought to be a glycolytic pathway, since CP level would not icrease greatly as opposed to the usage of cytochrome C (adrenaline-mediated heart failure, Tabl. 4). This assumption is apparent from a low capacity of the electron transport chain (due to cytochrome C deficiency).

As to ADP, its level tends to increase. As a result, if NAD is used only, the [ATP]/[ADP] ratio becomes low (Tabl. 2, 3, 4).

Thus, the administration of NAD or cytochrome C alone does not provide a steady state of the cellular energy transfer system (even if ATP returns to or approaches the normal). In addition, in both cases there will not occur the entire regeneration of cardiomyocyte ultrastructure (Tabl. 5).

As opposed to cytochrome C and NAD, the administration of inosine alone in allergic myocarditis (Tabl. 6)substantially provides the normalization of AMP and ADP levels, and not ATP. The level of these former, especially ADP (in case of using inosine in high dose of 160 mg/kg body weight) even is the normal above. With experimental coronary occlusion in dogs (Tabl. 7), there occur a considerable increase in ADP when using inosine in the optimum effective amount (80 mg/kg animal body weight), and again, no rise has been seen in the ATP not only at the region of circulatory insufficiency, and also at right-ventricular extraischemic area. As a result, when using inosine only, there takes place a further decrease in ATP/ADP ratio against the normal. (Tabl. 6,7). The rise in ADP and AMP becomes so significant that the total adenyl nucleotides will return to the normal, or even their level will be above-normal. This may be attributed to the fact that inosine has a pronounced effect on de novo adenyl nucleoide synthesis.

The above results idicate of the fact that none of inosine, cytochrome, or NAD to be used individually will return a normal steady state of the energy supply system in myocardial inflammations and coronary occlusion. The administration of the combined preparation of the invention,known under trade name ENERGOSTIM, which includes NAD, cytochrome C and inosine at their optimum mixture ratio,causes the complete normalization of all the parameters of cellular energy metabolism and the complete restoration of a homeostatic state of the complex energy transfer system in toxic and allergic myocarditis, that is it provides such effects which cannot be attained by using such agents individually (Tabl. 7, 8). If the action of "Energostim" was a simple summation over the effects, ADT would not be returned to the normal, and it would be the normal above by a factor of two or more. A similar situation would occur with other parameters of the energy transfer system.

With "Energostim" medication the increased ADP level, as it takes place when using inosine only, has not been seen.

If taken into account that ATP, ADP,AMP and CP, their ratios including $$\frac{[ATP]}{[ADP]}, \frac{[ADP][C][P]}{[ATP][CP][ADP]}$$

and NAD/NADH regulate (activate, inhibits) the rate of one or another process proceeding in the complex energy transfer system, the importance of homeostasis of such system is apparent. Moreover, the normal content of ATP and ADP makes it stable various cell structures and controls the status of the cotractile protein system.

Thus, for example ATP losses causes myocardial contraction, whereas a high level of ATP in the absence of Ca evokes its relaxation.

Cytochrome C (10 mg/kg), NAD (0,5 mg/kg) and inosine (80 mg/kg animal body weight) were mixed together and dissolved before its direct use in 5 ml of a commercially available normal saline which had been heated to 38°–40° C. under careful stirring.

The present invention will become more fully apparent from the following Examples of testing the claimed pharmaceutical composition.

EXAMPLE 1

Medicative Effect of Energostim in Toxic-Allergic Myocarditis (TAM)

(Mixture ratio: NAD 0.5 mg/kg, cytochrome C—10 mg/kg, inosine—80 mg/kg).

The tests were conducted on rabbits. TAM and AM were induced according to the methods of S. V. Andreev and M. V. Sokolov ("Modelirovanie zabolevany", Moskva, 1973). To initiate TAM 2 ml of horse blood serum were twice injected to animals intravenously every forth day, and 0.5 ml of staphylococcus toxin were injected seven days after the last injection of such serum.

A medicinal effect of Energostim in a 10-day TAM was recorded 5 days after the intravenous injection of the preparation in a dosage of 90.5 mg/g daily, beginning on the fifth day from the disease occurence. For comparison purposes of a medicinal effect of Energostim, cytochrom C was injected to animals also intravenously in a dosage of 10 mg/kg body weight at the same duration of the treatment period (Tabl. 11).

The degree and the nature of the action of the preparations in question on the oxygene and energy deficiency-associated conditions were judged from the levels of ATP, ADP, AMP, CP, the ATP/ADP ratio and the bioenergetic potential of adenyl nucleotides.

With a 10-day TAM, Energostim to be administered for 5-day period exibits a pronounced meditative effect, thereby giving rise to a complete normalization of the levels of adenyl nucleotides and their total content as well as the energetic potential and CP level of the system (Tabl. 8).

However, the administration of cytochrome C in a dosage of 10 mg/kg even within a 7 day-period does not provide the restoration of the whole capacity of the energy transfer system and its homeostatic state.

The regeneration of energy-rich sources in the complex energy transfer system together with making good myocardial blood supply gives rise to a considerable improvement in myocardial ultrastucture, a fast regression of an inflammatory process and a structural reparation of cardiac muscle.

This makes itself evident in the fact that there occur the decrease in volume of intracellular fluids, the mitochondrial occupation of spaces between myofibriles and increase in density of mitochondrial matrix. As a result, cellular mitochondria take ovoid shapes; the cristas increase in thick and return to the normal in quantity;- the mitochondrial membranes restore their original two-layered structural profile. In addition, there occur also the increase in quantity of glycogen granules; the rearrangment of Z-disks in a properly ordered fashion; a considerable decrease in quantity of the hypercontractilic sarcomeres; the reduction in dilatability of the sarcoplasmatic reticulum tubules.

As seen from the data of intracardiac hemodynamics, a considerable improvement in myocardial structure under exposure to Energostim gives rise to normalization of systolic and diaslolic functions with increasing systolic pressure and the rate of its rise to the normal, and with lowering the end diastolic load to the normal.

From the result obtained it may be concluded that Energostim by using it in energy depletion-associated conditions and in toxic-allergic miocarditis provides the entire restoration of myocardial energetics, the arresting of an inflammatory process, thereby increasing myocardial functional activity, and a considerable cutting the time to attain a stable therapeutical effect without danger of developing any intoxication.

EXAMPLE II

Medicative Effect of Energostim in Dog Acute Coronary Insufficiency (Mixture ratio: NAD-0.5 mg/kg, cytochrome C—10 mg/kg, inosine—80 mg/kg)

The acute coronary insufficiency was induced in mongrel dogs by deligation of the descending coronary branch at the upper tertile of it under etherizing the animals after anesthetic phentanyl-dimedrol-droperidol medication (Thionembutal anesthesia) with independent lung anesthesia using ventimask respirator OR-5. Energostim was injected to the animals in a dosage of 90.5 mg/kg body weight. Cytochrome C was injected in a dosage of 10 mg/kg.

INDUSTRIAL APPLICABILITY

The usage of an antihypoxic formulation of the invention, namely Energostim, provides the return of adenyl nucleotides and their ratios to the normal. In addition, there occur the normalization of CP at the extraischemic region and increase of it at the region of circulatory insufficiency by 29%, as compared with Control (Tabl. 9). The tension generated by the glycerinated myocardial fibrils under exposure to Energostim from the region of circulatory insufficiency is 1.74 times as high as Control, and yet it is still the normal below,with the tension generated from the extraischemic region rising to near-normal. This results in a considerable improvement in cardiomyocyte ultrastructure, the normalization of systolic pressure and the rate of lowering the left ventricular pressure as well as the rate of myocardial relaxation (Tabl. 10). As mentioned above in the case of myocarditis, the administration of cytochrome C solely causes the improvement in mitochondrial structure and the increase in ATP and CP, however it does not eliminate completely myocardial energy deficiency-associated conditions and provide the entire normalization of cardiac systolic and diastolic functions despite the fact that cytochrome C medication was conducted before initiating the coronary occusion.

TABLE 1

Levels of NAD and NAD-H in myocardial left ventricle in a 10-day TAM after treatment with NAD (0.5 mg/kg) and cytochrome C (5 mg/kg)(mcM/g of wet tissue)

| Groups, Subgroups | | NAD | NAD-H | Total | NAD-H/NAD |
|---|---|---|---|---|---|
| NORMAL (n = 8) | | $0.68 \pm 0.02$ | $0.36 \pm 0.04$ | $1.08 \pm 0.03$ | $0.50 \pm 0.036$ |
| Control (n = 8) | | $0.47 \pm 0.05***$ | $0.41 \pm 0.05$ | $0.84 \pm 0.03***$ | $0.86 \pm 0.04***$ |
| TAM TREATMENT | NAD 0.5 mg/kg (n = 5) | $0.68 + 0.04^{+++}$ | $0.33 \pm 0.015$ | $1.03 \pm 0.03^{+++}$ | $0.46 \pm 0.04^{+++}$ |
| | Cytochome C 5 mg/kg (n = 6) | $0.54 \pm 0.04***^x$ | $0.48 \pm 0.09$ | $1.05 \pm 0.07^+$ | $0.90 \pm 0.08^{xxx}$ |

Comparison to: normal *; control +; NAD medication in combination with cytochrome C - x
No symbol - not statistically significant.
One symbol - $P < 0.05$; two symbols - $P < 0.01$; three symbols - $P < 0.001$

TABLE 2

Effects of NAD/cytochrome C medication on myocardial right ventricular adenyl nucleotides in rabbits with a 10-day TAM

| Group, Subgroup | | | Statistical values | ATP | ADP | AMP | ATP/ADP | Total Nucleotides | Energetic Potential |
|---|---|---|---|---|---|---|---|---|---|
| Norm | n = 25 | 1 | $X\ m_x$ | 2.40 | 1.84 | 0.99 | 1.43 | 5.25 | 0.65 |
| | | | | 0.13 | 0.10 | 0.07 | 0.13 | 0.22 | 0.01 |
| | | 2 | $X \pm m_x$ | 1.67 | 1.51 | 0.87 | 1.27 | 3.77 | 0.60 |
| TAM | n = 20 | x | 0.12 | 0.10 | 0.08 | 0.10 | 0.34 | 0.01 |

TABLE 2-continued
Effects of NAD/cytochrome C medication on myocardial right ventricular adenyl nucleotides in rabbits with a 10-day TAM

| Group, Subgroup | | Statictical values | ATP | ADP | AMP | ATP/ADP | Total Nucleotides | Energetic Potential |
|---|---|---|---|---|---|---|---|---|
| NAD 0.25 mg/kg n = 9 | 3 | $X \pm m_x$ | 1.61 0.10 | 1.53 0.07 | 0.90 0.15 | 1.05 0.07 | 4.05 0.18 | 0.58 0.024 |
| NAD 0.5 mg/kg n = 8 | 4 | $X \pm m_x$ | 2.00 0.14 | 1.91 0,36 | 0.51 0.20 | 1.04 0.37 | 4.42 0.55 | 0.66 0.03 |
| Cytochrome C 5 mg/kg n = 9 | 5 | $X \pm m_x$ | 2.15 0.08 | 1.63 0.08 | 0.61 0.09 | 1.35 0.09 | 4.39 0.63 | 0.67 0.01 |
| | | $P_{1-2} <$ | 0.001 | — | — | — | 0.001 | 0.01 |
| | | $P_{1-3} <$ | 0.001 | 0.05 | — | 0.05 | 0.001 | 0,05 |
| | | $P_{1-4} <$ | — | — | 0.05 | — | 0.05 | — |
| | | $P_{1-5} <$ | — | — | 0.01 | 0.01 | — | — |
| | | $P_{2-3} <$ | — | — | — | — | — | — |
| | | $P_{2-4} <$ | — | — | — | — | — | — |
| | | $P_{2-5} <$ | 0.001 | — | 0.05 | — | — | 0.001 |
| | | $P_{3-4} <$ | 0.05 | — | — | — | — | — |
| | | $P_{4-5} <$ | — | — | — | — | — | — |

TABLE 3
Levels of adenyl nucleotides and CP (mcM/g wet tissue) in myocardial left ventricle in rabbits with a 10-day allergic myocarditis under effects NAD, cytochrome or inosine

| Group | | | ATP | ADP | AMP | ATP/ADP | Total nucleotides | Energy potential | CP |
|---|---|---|---|---|---|---|---|---|---|
| Norm (n = 25) | | | 2.5 ± 0.13 | 2.02 ±]0.12 | 1.07 ± 0.07 | 1.35 ± 0.07 | 5.52 ± 0.18 | 0.65 ± 0.02 | 3.40 ± 0.18 |
| | Control (n = 10) | | 1.68 ± 0.10* | 1.80 ± 0.17 | 0.85 ± 0.15 | 1.02 ± 0.14 | 4.41 ± 0.26* | 0.60 ± 0.02 | 1.95 ± 0.12* |
| MYO-CAR-DI-TIS | TREAT-MENT | NAD (n = 11) (0.5 mg/kg) | 2.46 ± 0.1$^x$ | 2.44 ± 0.11** | 0.92 ± 0.07 | 1.1 ± 0.12 | 5.48 ± 0.11 | 0.63 ± 0.03 | 3.01 ± 0.25$^x$ |
| | | Cytochrome C (n = 11) (10 mg/kg) | 3.19 ± 0.59$^x$ | 1.84 ± 0.15 | 0.89 ± 0.17 | 1.72 ± 0.65 | 5.92 ± 0.22 | 0.73 ± 0.03 | 2.87 ± 0.35$^x$ |
| | | Inosine (n = 6) (80 mg/kg) | 2.66 ± 0.13$^x$ | 1.90 ± 0.10 | 0.99 ± 0.05 | 1.82 ± 0.18 | 5.55 ± 0.17 | 0.66 ± 0.01 | |

Comparison to: norm *; control x; P is not above than 0.05

TABLE 4
Levels of adenyl nucleotides and CP (mcM/g wet tissue) in myocardial left ventricle in rabbit with a 3-day adrenaline-mediated heart failure under effect NAD (0.5 mg/kg) and cytochrome (10 mg/kg)

| Group | | | ATP | ADP | AMP | ATP/ADP | Total nucleotides | Energy potential | CP |
|---|---|---|---|---|---|---|---|---|---|
| Normal (n = 25) | | | 2.5 ± 0.13 | 2.02 ± 0.12 | 1.07 ± 0.07 | 1.35 ± 0.07 | 5.52 ± 0.18 | 0.65 ± 0.02 | 3.40 ± 0.1 |
| | Control (n = 14) | | 1.62 ± 0.25* | 1.18 ± 0.20* | 0.85 ± 0.13 | 1.85 ± 0.34* | 3.65 ± 0.47* | 0.61 ± 0.06 | 1.54 ± 0.03* |
| MYO CAR DI-TIS | TREAT-MENT | NAD (n = 18) (0.5 mg/kg) | 2.62 ± 0.29$^x$ | 2.61 ± 0.48$^x$ | 0.92 ± 0.13 | 1.36 ± 0.33 | 6.17 ± 0.72$^x$ | 0.64 ± 0.72 | 3.01 ± 0.23$^x$ |
| | | Cyto-chrome C (n = 11) (10 mg/kg) | 2.3 ± 0.14$^x$ | 1.84 ± 0.10$^x$ | 0.87 ± 0.05$^x$ | 1.25 ± 0.11* | 5.05 ± 0.13$^x$ | 0.63 ± 0.02 | 2.93 ± 0.35$^x$ |

Comparison to: normal *; control x; P is not more than 0.05

TABLE 5
Quantitative determination of mitochondia (MC) in left ventricle on photoelectronograms (PEG) in normal rabbits, rabbits with experimental 10-day TAM and rabbits with TAM under NAD (0.5 mg/kg) and cytochrome C (5 mg/kg) medications

| | | TAM | | |
|---|---|---|---|---|
| Value | Mormal rabbits (n = 8) | Control (n = 3) | NAD (0.5 mg/kg) (n = 3) | Cytochrome C (6 mg/kg) (n = 3) |
| Number of MC per PEG | 20.2 ± 0.72 | 7.0 ± 0.48*** | 10.35 ± 2.12** | 12.26 ± 1.11**++ |
| Number of cristas per per PEG | 193.5 +24.7 | 27.0+4.0 | 65.4 +5.6 | 56.4 +1.81 |

TABLE 5-continued

Quantitative determination of mitochondia (MC) in left ventricle
on photoelectronograms (PEG) in normal rabbits, rabbits with
experimental 10-day TAM and rabbits with TAM under NAD (0.5 mg/kg)
and cytochrome C (5 mg/kg) medications

| Value | Mormal rabbits (n = 8) | TAM Control (n = 3) | NAD (0.5 mg/kg) (n = 3) | Cytochrome C (6 mg/kg) (n = 3) |
|---|---|---|---|---|
| Density of distribution of MC on PEG (mcm) | 3.96 ± 0.25 | 5.46 ± 0.5*** | 5.0 ± 0.20* | 4.64 ± 1.19* |
| Size of a single MC (mcm) | 0.15 ± 0.019 | 0.66 ± 0.13*** | 0.5 ± 0.062** | 0.38 ± 0.014***+ |
| Number of cristas in a single MC | 10.0 ± 0.27 | 4.0 ± 0.57*** | 5.2 ± 0.9** | 4.6 ± 2.64* |
| Index of MC energy efficiency (IMEE) | 766 ± 55 | 191 ± 38*** | 354 ± 54.7**+ | 334.4 ± 23.47**++ |

Comparison to: normal *; control +; $P < 0.05$ -one symbol.
$P < 0.01$ - two symbols. $P < 0.001$ - three symbols

TABLE 6

Adenyl nucleotides levels in rabbit heart in experimental
10-day allergic myocarditis under effect inosine

| Groups | | | ATP | ADP | AMP | Total | Energy potential | ATP/ADP |
|---|---|---|---|---|---|---|---|---|
| | | | | | | Left ventricle | | |
| Normal | | (n = 1) 1 | 3.23 ± 0.09 | 1.49 ± 0.09 | 0.71 ± 0.13 | 5.36 ± 0.12 | 0.73 ± 0.72 | 2.23 ± 0.18 |
| MYOCAR-DITIS | TREAT-MENT | Control (n = 7) 2 | 1.51 ± 0.09 | 1.27 ± 0.13 | 0.69 ± 0.08 | 3.48 ± 0.20 | 0.62 ± 0.02 | 1.26 ± 0.13 |
| | | Inosine 80 mg/kg ( = 6) 3 | 2.66 ± 0.13 | 1.50 ± 0.10 | 0.99 ± 0.05 | 5.14 ± 0.17 | 0.66 ± 0.01 | 1.82 ± 0.18 |
| | | Inosine 160 mg/kg (n = 8) 4 | 2.99 ± 0.11 | 2.36 ± 0.15 | 0.98 ± 0.16 | 6.20 ± 0.31 | 0.65 ± 0.02 | 1.25 ± 0.12 |
| Significance of variationa between groups (P) | | $P_{1-2}$ | 0.001 | — | — | 0.001 | 0.001 | 0.001 |
| | | $P_{2-3}$ | 0.001 | — | 0.01 | 0.001 | — | 0.05 |
| | | $P_{2-4}$ | 0.001 | 0.001 | — | 0.001 | — | — |
| | | $P_{1-3}$ | — | 0.01 | — | 0.02 | — | 0.02 |
| | | $P_{1-4}$ | 0.01 | — | — | — | — | — |
| | | $P_{3-4}$ | — | 0.001 | — | 0.02 | — | 0.01 |
| | | | | | | Right ventricle | | |
| Normal | | (n = 1) 1 | 2.75 ± 0.26 | 1.47 ± 0.17 | 0.74 ± 0.03 | 4.89 ± 0.43 | 0.68 ± 0.02 | 1.86 ± 0.18 |
| MYOCAR-DITIS | TREAT-MENT | Control (n = 7) 2 | 1.33 ± 0.12 | 1.24 ± 0.16 | 0.73 ± 0.05 | 3.29 ± 0.26 | 0.59 ± 0.01 | 1.15 ± 0.09 |
| | | Inosine 80 mg/kg ( = 6) 3 | 2.25 ± 0.14 | 1.74 ± 0.21 | 0.63 ± 0.08 | 4.82 ± 0.29 | 0.65 ± 0.01 | 0.41 ± 0.21 |
| | | Inosine 160 mg/kg (n = 8) 4 | 2.22 ± 0.20 | 1.85 ± 0.25 | 0.96 ± 0.06 | 9.96 ± 0.23 | 0.63 ± 0.02 | 1.39 ± 0.30 |
| Significance of variationa between groups (P) | | $P_{1-2}$ | 0.001 | — | — | 0.01 | 0.01 | 0.01 |
| | | $P_{2-3}$ | 0.001 | — | — | 0.01 | 0.05 | — |
| | | $P_{2-4}$ | 0.01 | | | | | |
| | | $P_{1-3}$ | — | 0.05 | 0.01 | 0.001 | — | — |
| | | $P_{1-4}$ | — | — | — | — | — | — |
| | | $P_{3-4}$ | — | — | — | — | — | — |

TABLE 7

Effects of inosine (80 mg/kg) on myocardial energy metabolism in
experimental a 2-2.5-hour coronary occlusion in dogs. ($X \pm m_x$)

| Group, soubgroup | mcmole/g wet tissue | | | | | |
|---|---|---|---|---|---|---|
| | AdT | ADP | AdT + ADP + AMP | Energy potential | ADT/ADP | |
| Normal animal n = 6 | 3.62 ± 0.22 | 1.73 ± 0.22 | 6.19 ± 0.37 | 0.72 ± 0.02 | 2.27 ± 0. | |

TABLE 7-continued

Effects of inosine (80 mg/kg) on myocardial energy metabolism in experimental a 2-2.5-hour coronary occlusion in dogs, ($X \pm m_x$)

| Group, soubgroup | | | AdT | ADP | AdT + ADP + AMP | Energy potential | ADT/ADP |
|---|---|---|---|---|---|---|---|
| CORONARY | Zone of ischemia | Control n = 8 | 2.29 ± 0.20* | 1.29 ± 0.09 | 413 ± 0.30* | 0.71 ± 0.02 | 1.77 ± 0. |
| | | Inosine n = 14 | 2.36 ± 0.12* | 2.31 ± 0.19* | 5.55 ± 0.25+ | 0.64 ± 0.01*+ | 1.14 ± 0.* |
| OCCLUSION | Extra ischemic zone | Control n = 8 | 2.38 ± 0.16* | 1.49 ± 0.10 | 4.45 ± 0.32* | 0.70 ± 0.01 | 1.62 ± 0. |
| | | Inosine n = 14 | 2.22 ± 0.60* | 2.40 ± 0.19*+ | 5.51 ± 0.32* | 0.63 ± 0.01*+ | 0.99 ± 0.* |

Note:
comparison to normal *; control +; P < is not more than

TABLE 8

Effects of Energostim on levels of adenyl nucleotides and CP in a 10-day TAM, (mcM/g wet tissue)

| Group, subgroup | Statistic value | ATP | ADP | AMP | $P_n$ | ATP/ADP | Total nucleotides | Phosphorylation potential | CP |
|---|---|---|---|---|---|---|---|---|---|
| Normal | $M \pm m_x$ | 3.11 ± 0.18 6 | 2.1 ± 0.44 6 | 0.67 ± 0.10 6 | 2.21 ± 0.19 5 | 1.5 ± 0.09 6 | 5.88 ± 0.41 6 | 1.48 ± 0.21 5 | 3.26 ± 0.14 6 |
| Control (10-day TAM | $M \pm m_x$ | 1.82 ± 0.07* 9 | 1.57 ± 0.07* 3 | 0.84 ± 0.03 9 | 2.26 ± 0.07 5 | 1.1 ± 0.08* 9 | 4.24 ± 0.08* 9 | 2.10 ± 0.37* 5 | 1.69 ± 0.23* 7 |
| Treatment by using Energostim 90.5 mg/kg | $M \pm m_x$ | 3.03 ± 0.07* 11 | 2.30 ± 0.07* 11 | 0.74 ± 0.072$^x$ 11 | 2.23 ± 0.15 7 | 1.53 ± 0.07$^x$ 11 | 5.82 ± 0.21$^x$ 11 | 1.56 ± 0.17$^x$ 7 | 3.12 ± 0.095$^x$ 7 |

Comparison of standard deviations to: normal *; control x; P is not more than 0.05

TABLE 9

Effects of Energostim on level, of adenyl nucleotides, CP and contractile force of the isolated contractile protein system in dog acute coronary insufficiency

| Group | | ATP | ADP | AMP | CP | Energy potential | Tension, mH/mm |
|---|---|---|---|---|---|---|---|
| Control I (n = 8) | | 4.15 ± 0.45 | 2.26 ± 0.50 | 0.34 ± 0.04 | 3.24 ± 0.23 | 0.70 ± 0.09 | 28.8 ± 2.2 |
| Control II 10-min CO n = 3 | Zone | 4.75 ± 0.55 | 2.48 ± 0.35 | 0.30 ± 0.02 | 1.60 ± 0.20* | 0.80 ± 0.15 | 9.8 ± 1.5* |
| | Out of zone | 4.57 ± 0.45 | 2.27 ± 0.15* | 0.31 ± 0.05 | 1.25 ± 0.17* | 0.79 ± 0.14 | 16.6 + 2.3* |
| Control III 2-hour CO n = 10 | Zone | 2.97 ± 0.29* | 1.69 ± 0.17*+ | 0.95 ± 0.12* | 1.40 ± 0.10* | 0.68 ± 0.02 | 11.5 ± 2.3* |
| | Out of zone | 3.8 ± 0.27 | 1.29 ± 0.22* | 0.80 ± 0.06* | 2.32 ± 0.10*+ | 0.73 ± 0.04 | 15.8 ± 1.3* |
| Treatment by using Energostim n = 5 | Zone | 4.20 ± 0.25 | 2.30 ± 0.15 | 0.30 ± 0.02 | 1.80 ± 0.10** | 0.76 ± 0.06 | 17.1 ± 2.3*+* |
| | Out of zone | 4.10 ± 0.15 | 2.2 ± 0.27 | 0.30 ± 0.01 | 3.34 ± 0.17+* | 0.80 ± 0.12 | 22.4 ± 3.6$^x$ |

Note:
Comparison to Control I *; II +; III x. Statistically significant P < 0.01 and less.

TABLE 10

Effects of Energostim on extracardiac hemodynamics in acute myocardial ischemia in dogs

| Group | HRT | SBP | $d_p/dt_{max}$ | $d_p/dt_{min}$ | CWI | SP | EDP | RI |
|---|---|---|---|---|---|---|---|---|
| Control I n = 8 | 167 ± 10 | 75 ± 5 | 1373 ± 142 | 1372 ± 108 | 20.3 ± 1.6 | 140 ± 15 | 8.3 ± 0.3 | 14.6 ± 2.2 |
| Control II 15-min CO n = 3 | 176 ± 17 | 64 ± 5* | 1248 ± 153 | 1057 ± 170 | 22.5 ± 2.6 | 134 ± 22 | 8.6 ± 0.6 | 12.3 ± 1.6 |
| Control III 2-hour CO n = 5 | 171 ± 14 | 65 ± 1* | 1250 ± 138 | 990 ± 159* | 22.4 ± 2.2 | 174 ± 7.5 | 7.4 ± 0.6 | 9.8 ± 1.9* |
| Treatment using Energostim | 180 ± 17 | 75 ± 8+$^x$ | 1663 ± 324 | 1140 ± 149 | 24.3 ± 3.7 | 156 ± 13 | 8.4 ± 0.4 | 12.0 ± 2.3 |

TABLE 10-continued

| | Effects of Energostim on extracardiac hemodynamics in acute myocardial ischemia in dogs | | | | | | | |
|---|---|---|---|---|---|---|---|---|
| Group | HRT | SBP | $d_p/dt_{max}$ | $d_p/dt_{min}$ | CWI | SP | EDP | RI |
| 90.5 mg/kg n = 5 | | | | | | | | |

Note: Comparison to Control I *; Control II ÷; Control III x

TABLE 11

| | Comparison of Energostim activity to Cytochrome C | | | | | | | |
|---|---|---|---|---|---|---|---|---|
| | | Control Energostim | | | | Prior art, Cytochrome C | | |
| Ingredients | Nicotinamide adenine dinucleotide (NAD) | — | 0.25 | 0.5 | 5 | — | — | — |
| | Cytochrome C | — | 5 | 10 | 15 | 5 | 10 | 15 |
| | Inosine | — | 20 | 80 | 250 | — | — | — |
| Effects on energy metabolism, (% based on normal) | ATP | 58 | 90.5 | 97.4 | 92.5 | 77.2 | 83.3 | 86.3 |
| | ADP | 47.6 | 98.6 | 109.5 | 153.4 | 88.6 | 59.2 | 53.8 |
| | AMP | 95.5 | 90.9 | 110.4 | 138 | 61.6 | 63.6 | 62.0 |
| | ATP/ADP | 73.3 | 94.4 | 102 | 93.2 | 94.4 | 149.7 | 148 |
| | CP | 51.8 | 80.8 | 95.7 | 85.6 | 114.2 | 131.9 | 134 |
| | NAD | 69.1 | — | 100.0 | 85.6 | 114.2 | 131.9 | 134 |
| | NADH | 143.9 | — | 91.7 | — | 133.3 | — | — |
| | [NAD H]/[NAD] | 172 | 90.5 | 103.5 | 125 | 180.0 | — | — |

Note: 100% expresses adenyl nucleotide level. CP and NADH/NAD in rabbit myocardium is without abnormalities. Toxic and allergic myocarditis with expressed energy deficiency

We claim:

1. An antihypoxic formulation comprising cytochrome C, characterized in that it further includes nicotinamide adenine dinucleotide and inosine at the following mixture ratio (parts by weight):

cytochrome C 5-15
nicotinamide adenine dinucleotide 0.5-5
inosine (riboxin) 20-250.

* * * * *